(12) United States Patent
Lia et al.

(10) Patent No.: US 10,226,183 B2
(45) Date of Patent: *Mar. 12, 2019

(54) DEVICES AND METHODS FOR TEMPERATURE DETERMINATION

(71) Applicant: Welch Allyn, Inc., Skaneateles Falls, NY (US)

(72) Inventors: Raymond A. Lia, Auburn, NY (US); Robert J. Wood, Syracuse, NY (US); David E. Quinn, Auburn, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 861 days.

This patent is subject to a terminal disclaimer.

(21) Appl. No.: 14/144,989

(22) Filed: Dec. 31, 2013

(65) Prior Publication Data

US 2014/0221796 A1    Aug. 7, 2014

Related U.S. Application Data

(63) Continuation of application No. 12/958,670, filed on Dec. 2, 2010, now Pat. No. 8,657,758.

(51) Int. Cl.
| | |
|---|---|
| *A61B 5/01* | (2006.01) |
| *A61B 5/024* | (2006.01) |
| *A61B 5/1455* | (2006.01) |
| *A61B 5/00* | (2006.01) |

(52) U.S. Cl.
CPC ............ *A61B 5/01* (2013.01); *A61B 5/02433* (2013.01); *A61B 5/14552* (2013.01); *A61B 5/6833* (2013.01); *Y10T 29/49002* (2015.01)

(58) Field of Classification Search
CPC .............................. A61B 5/01; A61B 5/14552
See application file for complete search history.

(56) References Cited

U.S. PATENT DOCUMENTS

| | | | |
|---|---|---|---|
| 4,138,889 A | 2/1979 | Fraschini | |
| 5,678,566 A | 10/1997 | Dribbon | |
| 5,725,308 A | 3/1998 | Smith et al. | |
| 6,220,750 B1 | 4/2001 | Palti | |

(Continued)

FOREIGN PATENT DOCUMENTS

| | | |
|---|---|---|
| GB | 1344206 A | 1/1974 |
| GB | 2289684 A | 8/1995 |

OTHER PUBLICATIONS

Finvers et al., "Wireless temporal artery bandage thermometer," Biomedical Circuits and Systems Conference, 2006. BioCAS 2006. IEEE, Nov. 29, 2006-Dec. 1, 2006, pp. 166-169.

(Continued)

*Primary Examiner* — Rene Towa
*Assistant Examiner* — H. Q. Nguyen
(74) *Attorney, Agent, or Firm* — Lee & Hayes, P.C.

(57) ABSTRACT

A temperature determination method includes temporarily contacting a forehead of a subject with a first surface of a removable patch, and exposing a second surface of the patch opposite the first surface to ambient conditions. The method also includes sensing a temperature of the first surface of the patch while the first surface is in contact with the forehead at a first location thereon, sensing a temperature of the second surface of the patch, and calculating a sub-skull temperature of the subject based on the sensed temperatures of the first and second surface.

26 Claims, 5 Drawing Sheets

(56) References Cited

U.S. PATENT DOCUMENTS

| | | | |
|---|---|---|---|
| 6,257,759 | B1 | 7/2001 | Witonsky et al. |
| 6,292,685 | B1 | 9/2001 | Pompei |
| 6,604,854 | B1 | 8/2003 | Limburg et al. |
| 6,929,611 | B2 | 8/2005 | Koch |
| 7,249,883 | B2 | 7/2007 | Kuroda et al. |
| 7,625,117 | B2 | 12/2009 | Haslett et al. |
| 2002/0105436 | A1 | 8/2002 | Bell et al. |
| 2003/0210146 | A1 | 11/2003 | Tseng |
| 2004/0019293 | A1* | 1/2004 | Schweitzer, Jr. .. A61B 5/14552 600/549 |
| 2005/0070776 | A1* | 3/2005 | Mannheimer .......... A41D 20/00 600/340 |
| 2005/0280531 | A1 | 12/2005 | Fadem et al. |
| 2006/0052677 | A1 | 3/2006 | Yu |
| 2006/0122473 | A1 | 6/2006 | Kill et al. |
| 2007/0177651 | A1 | 8/2007 | Daugherty et al. |
| 2008/0071189 | A1* | 3/2008 | Yarden ................... A61B 5/01 600/549 |
| 2008/0091090 | A1 | 4/2008 | Guillory et al. |
| 2009/0141773 | A1 | 6/2009 | Lin et al. |
| 2009/0187115 | A1 | 7/2009 | Yarden et al. |
| 2009/0306536 | A1* | 12/2009 | Ranganathan .......... A61B 5/01 600/549 |

OTHER PUBLICATIONS

Harioka et al. "'Deep-forehead' temperature correlates well with blood temperature," Canadian Journal of Anesthesia, vol. 47, No. 10, pp. 980-983.

Mangat et al., "A comparison of technologies used for estimation of body temperature," Physiological Measurement Create an alert RSS this journal, vol. 31, No. 9, 2010, pp. 1105-1118.

"How does Pulse oximetry work?" Retrieved Jan. S, 2011 from: ht1p:liwww.creaghbrown.co.uklanae/]2ulsox.btm (6 pages).

International Search Report and Written Opinion for International Application No. PCTIUS2008/068004, dated Jan. 20, 2009 (12 pages).

International Search Report for International Application No. PCTIUS200SI038936, dated May 4, 2006, (3 pages).

SP02 Monitoring Application Note, Philips Electronics North America Corporation, Copyright 2003, Published Jan. 2003, Edition 2 (6 pages).

* cited by examiner

DEVICES AND METHODS FOR TEMPERATURE DETERMINATION

CROSS-REFERENCE TO RELATED APPLICATIONS

This Application is a continuation of U.S. patent application Ser. No. 12/958,670, filed Dec. 2, 2010, the entire disclosure of which is incorporated herein by reference.

STATEMENT REGARDING FEDERALLY SPONSORED RESEARCH OR DEVELOPMENT

None.

REFERENCE TO A "SEQUENCE LISTING"

Not applicable.

BACKGROUND OF THE INVENTION

Field of the Invention

The present disclosure generally relates to devices and methods for temperature determination and, in particular, to devices and methods for calculating a sub-skull temperature.

Description of Related Art

Internal body temperature is widely used by physicians and other healthcare professionals as an indicator of a person's health. In most healthcare facilities, various non-invasive techniques may be utilized to measure internal temperature before, during, and/or after treatment. Such techniques typically include the use of oral, rectal, tympanic, or axial thermometers. These instruments are useful in providing a substantially instantaneous temperature reading, but are not generally used to provide continuous, relatively long-term monitoring of a patient's temperature. However, it is this continuous temperature measurement, or the determination of relatively sudden changes in patient temperature that is most useful to healthcare professionals when providing treatment. Such devices are not well-suited for continuous temperature measurement since, for example, disposing a thermometer in the mouth of a patient for long periods of time can cause discomfort and can be otherwise cumbersome. Moreover, often the condition of the patient may make it difficult or impossible to access, for example, the mouth, rectum, and/or other areas of the body where temperature is typically measured with such devices.

To overcome some of these problems, devices have been developed enabling continuous monitoring of patient temperature. Such devices are typically in the form of an adhesive patch or bandage-like structure having an array of temperature sensors. Such devices are typically adhered to the patient's skin overlaying a portion of the temporal artery. These devices, however, are characterized by deficiencies making them undesirable for use in many patient treatment settings. For example, such devices must be placed in close proximity to the temporal artery in order to obtain an accurate temperature measurement. However, since the temporal artery is beneath the skin, and is not easily visible, such devices are often mispositioned on the patient. Such mispositioning can have adverse affects on the accuracy of the temperature measurement obtained using such devices. In addition, the temperature at the skin surface can be significantly influenced by the ambient temperature and often does not correlate well with core body temperature. Moreover, reducing the number of sensors employed in the sensor arrays of such devices reduces the accuracy of the body temperature estimation while increasing the number of sensors increases the cost of such devices.

The exemplary embodiments of the present disclosure overcome one or more of the deficiencies described above.

BRIEF SUMMARY OF THE INVENTION

In an exemplary embodiment of the present disclosure, a temperature determination method includes (a) temporarily contacting a forehead of a subject with a first surface of a removable patch, and exposing a second surface of the patch opposite the first surface to ambient conditions. The method also includes (b) sensing a temperature of the first surface of the patch while the first surface is in contact with the forehead at a first location thereon, (c) sensing a temperature of the second surface, and (d) calculating a sub-skull temperature of the subject based on the sensed temperatures of the first and second surface.

In such an exemplary embodiment, the calculated sub-skull temperature is based on an estimated thermal resistance of the subject's skull and forehead skin, and the thermal resistance is estimated based on at least one of an age, weight, and gender of the subject.

In other exemplary embodiments, the temperatures of the first and second surfaces are sensed substantially simultaneously, the calculated sub-skull temperature is based on a known thermal resistance of the patch, and the patch comprises a first temperature sensor associated with the first surface and a second temperature sensor associated with the second surface.

In additional exemplary embodiments, the method also includes calculating a plurality of sequential sub-skull temperatures by repeating steps (b) through (d), at a desired interval, for a predetermined period of time. In such an exemplary embodiment, the method also includes comparing the plurality of sub-skull temperatures to a predetermined threshold temperature and triggering an alarm in response to the comparison. The method also includes calculating a sub-skull temperature change rate, comparing the sub-skull temperature change rate to a predetermined threshold change rate, and triggering an alarm in response to the comparison.

In a further exemplary embodiment, the method further includes sensing a blood flow metric, the metric indicative of blood flow at the forehead skin proximate the first surface, and comparing the sensed metric to a predetermined metric threshold. In such an exemplary embodiment, the method includes repositioning the patch to a second location on the forehead of the subject in response to the comparison. The metric may be a change in infrared light transmissivity through the skin of the forehead. In another exemplary embodiment, sensing the metric includes passing radiation of a known wavelength through the subject's forehead skin, and detecting the radiation proximate the first surface. In such an exemplary embodiment, the metric may be a difference in temperature sensed across the first surface.

The still another exemplary embodiment of the present disclosure, the method includes maintaining the patch at the first location in response to the comparison of the metric and the metric threshold. Such a method also includes calculating the sub-skull temperature using a correction factor corresponding to the metric, wherein the correction factor is indicative of heat flow through the forehead skin. In such a method, the metric may be arterial pulse intensity and the correction factor is generated based on the metric. In such a method, the metric may also be a temperature difference sensed across the first surface of the patch and the correction factor is generated based on the metric.

In an additional exemplary embodiment, sensing the metric includes substantially simultaneously sensing temperature at a plurality of locations along the first surface, and calculating the sub-skull temperature includes determining a maximum difference between the temperatures sensed at the plurality of locations.

In a further exemplary embodiment of the present disclosure, a method of temperature determination includes removably attaching a first surface of a patch to a forehead of a subject, and exposing a second surface of the patch opposite the first surface to ambient conditions, substantially simultaneously sensing a temperature of the first and second surfaces while the first surface is attached to the forehead, and calculating a sub-skull temperature of the subject based on the sensed temperatures and an estimated thermal resistance of the subject's skull and forehead skin.

In such an exemplary embodiment, the calculated sub-skull temperature is based on a known thermal resistance of the patch, and the method further includes sensing a metric indicative of blood flow at the forehead skin proximate the first surface, and calculating the sub-skull temperature based on the metric.

In such an exemplary embodiment, the metric is a change in infrared light transmissivity through the skin of the forehead, and sensing the metric includes passing radiation of a known wavelength through the subject's forehead skin and detecting the radiation proximate the first surface. In additional exemplary embodiments, the metric includes a temperature gradient sensed across the first surface.

In another exemplary embodiment of the present disclosure, a temperature determination device includes a patch defining a first surface and a second surface opposite the first surface, the first surface is removably attachable to a forehead of a subject. The device further includes a first sensor positioned to detect a temperature of the first surface while the patch is attached to the forehead, and a second sensor positioned to detect a temperature of the second surface while the patch is attached to the forehead.

In such an exemplary embodiment, the device further includes a controller operably connected to the first and second sensors and configured to calculate a sub-skull temperature based on the detected temperatures of the first and second surfaces, an estimated thermal resistance of the subject's skull and forehead skin, and a known thermal resistance of the patch.

In an additional exemplary embodiment, the device includes an infrared radiation source and a third sensor configured to detect radiation emitted by the source and passing through the subject's forehead skin.

In yet another exemplary embodiment of the present disclosure, a temperature determination method includes removably attaching a first surface of a patch to a forehead of a subject, and exposing second and third surfaces of the patch opposite the first surface to ambient conditions. In such a method, the second surface is separated from the first surface by a first patch thickness, and the third surface is separated from the first surface by a second patch thickness different than the first thickness. The method also includes sensing a temperature of the second and third surfaces while the first surface is attached to the forehead, and calculating a sub-skull temperature of the subject based on the sensed temperatures of the second and third surfaces, and an estimated thermal resistance of the subject's skull and forehead skin.

In such an exemplary embodiment, the first thickness is characterized by a first thermal resistance, and the second thickness is characterized by a second thermal resistance different than the first resistance, and the method also includes calculating the sub-skull temperature based on the first and second thermal resistances. Such an exemplary method also includes sensing the temperature of the second and third surfaces with a non-contact infrared sensing device.

DETAILED DESCRIPTION OF THE INVENTION

Figure 1:
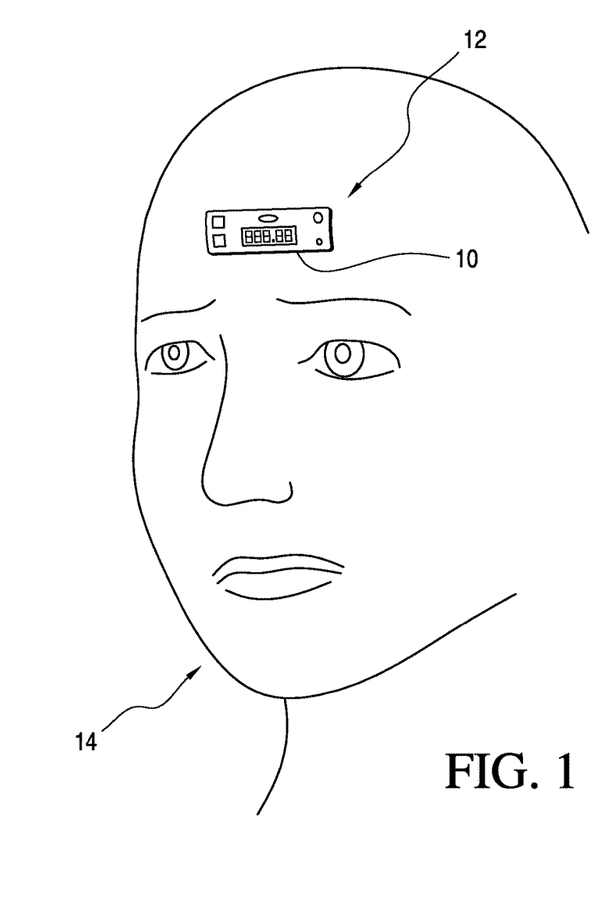
FIG. 1 illustrates a patch positioned on a forehead of a subject according to an exemplary embodiment of the present disclosure.
Figure 2:
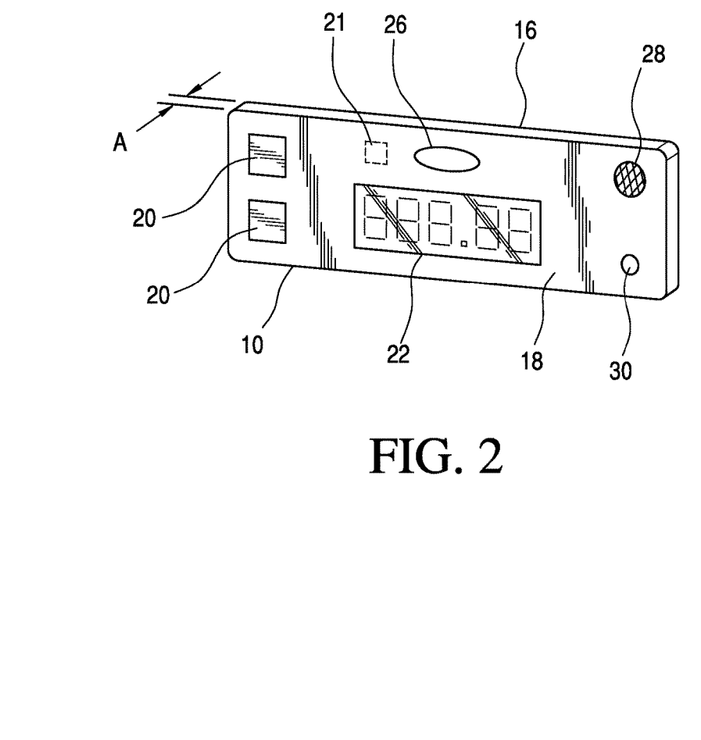
FIG. 2 illustrates a patch according to an exemplary embodiment of the present disclosure.
Figure 3:
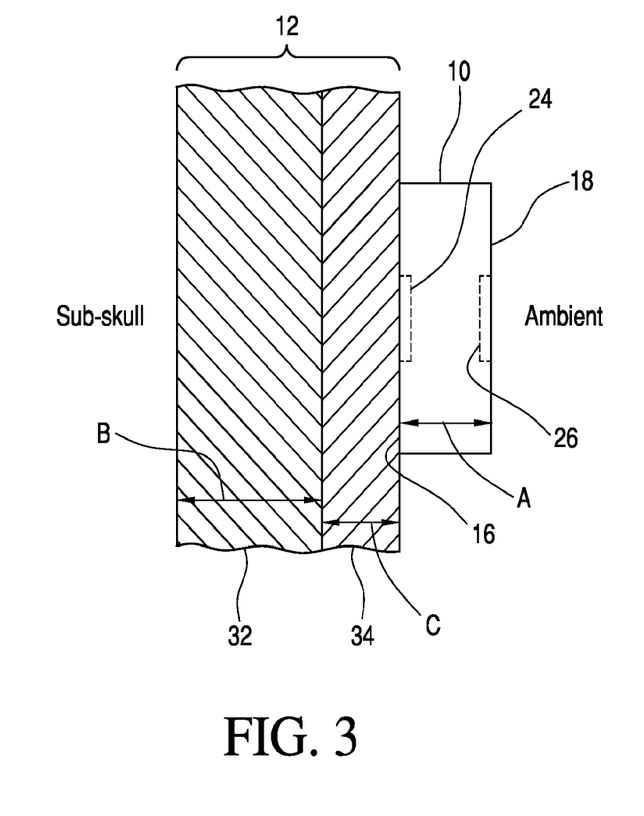
FIG. 3 illustrates a partial cross-section of a forehead of the subject with a patch connected thereto, according to an exemplary embodiment of the present disclosure.

FIGS. 1-8 illustrate exemplary temperature measurement devices and/or patches 10 useful in determining the temperature of a subject 14. Such subjects 14 may be, for example, human beings in need of medical treatment or diagnosis. As shown in FIG. 1, a patch 10 of the present disclosure may be connected, affixed, disposed, adhered, and/or otherwise connected to a forehead 12 of the subject 14. For example, the patch 10 may be temporarily connected to and/or may temporarily contact at least a portion of the forehead 12 during use. Positioning the patch 10 on the forehead 12 of the subject 14 may be advantageous when determining a temperature of the subject 14 since the forehead 12 is relatively isolated from veins, arteries, and/or other blood flow passages. The flow of blood through such anatomical structures may cause error in temperature measurements and may make it more difficult to calculate, for example, a sub-skull temperature of the subject 14. The sub-skull temperature of the subject 14 may be, for example, a core temperature and/or any other like internal body temperature of the subject 14. For example, the sub-skull temperature may comprise the internal temperature of the subject 14 distal to the frontal portion of the skull. As referred to herein, the forehead 12 may comprise the frontal skull bone 32 and the layer of skin 34 positioned proximal and/or overlaying the skull bone 32 (FIG. 3).

As shown in FIG. 2, an exemplary embodiment of the patch 10 may include one or more components configured to assist in calculating a sub-skull temperature based on a measurement of heat flow. For example, the patch 10 may include one or more operator interfaces 20. Such operator interfaces 20 may include one or more buttons, switches, keypads, dials, knobs, and/or other like devices configured to assist in controlling one or more functions of the patch 10. Such operator interfaces 20 may be useful in, for example, energizing and/or deenergizing one or more components of the patch 10, toggling through and/or selecting one or more modes of operation or display, enabling and/or disabling one or more alarms or signals associated with patch operation, initiating a single instantaneous sub-skull temperature calculation, initiating a substantially continuous and/or repeating sub-skull temperature calculation, and/or other like modes, functions, or operations.

In an exemplary embodiment, the patch 10 may include one or more controllers 21, and each of the operator interfaces 20 may be functionally, operably, electrically, and/or otherwise connected to the controller 21. At least one of the additional components of the patch 10 may also be similarly connected to the controller 21, and the controller 21 may be configured to control the operation of each such component. In an exemplary embodiment, the controller 21 may be configured to receive signals, information, measurements, and/or other data from one or more sensors of the patch 10, and to calculate a sub-skull temperature of the subject 14 based on the information received. The controller 21 may also be configured to execute one or more commands and/or control programs. For example, the controller 21 may be programmed to initiate one or more alarms in response to calculating a sub-skull temperature that is greater than or equal to a predetermined threshold temperature. In addition, the controller 21 may be configured to initiate such an alarm during a substantially continuous sub-skull temperature calculation operation if the calculated sub-skull temperature increases and/or decreases at a rate that is greater than or equal to a predetermined threshold temperature change rate. In such an embodiment, the controller 21 may substantially continuously calculate a sub-skull temperature change rate, and the threshold temperature and/or the threshold temperature change rate may be indicative of the onset of infection and/or of a decline in the health of the subject 14. In an exemplary embodiment, such a threshold temperature may be approximately 100° F. and such a threshold change rate may be approximately 0.5° F./minute. The controller 21 may also initiate such an alarm to indicate that a location of the patch 10 should be changed, and such a location change alarm may be initiated in response to one or more sensed metrics indicative of blood flow at the forehead skin 34.

In an exemplary embodiment, the patch 10 may also include one or more displays 22. The display 22 may be, for example, a liquid crystal diode (LCD) screen, a light emitting diode (LED) display, a digital read-out, and/or any other like display device. The display 22 may be configured to, for example, indicate the calculated sub-skull temperature of the subject 14 during operation of the patch 10. The display 22 may be configured to display the calculated sub-skull temperature substantially instantaneously and/or substantially continuously depending on the mode of operation of the patch 10. The display 22 may also be configured to indicate the mode of operation of the patch 10 (for example, continuous or instantaneous modes of sub-skull temperature calculation), as well as whether one or more threshold temperatures, threshold temperature change rates, and/or sensed blood flow metric thresholds have been met or exceeded. As shown in FIGS. 1 and 2, the display 22 may be, for example, a substantially numerical digital display, and may also be configured to display any other typical operating information such as, for example a temperature vs. time trend line or other graphical depiction.

The patch 10 may also include one or more signal devices 28. Such signal devices 28 may include, for example, one or more lights, LEDs, speakers, sirens, and/or other like devices configured to emit an audible and/or optical alarm or signal in response to a command or signal from the controller. As described above, such an alarm or other signal may be initiated by, for example, the controller when the calculated sub-skull temperature meets or exceeds a threshold sub-skull temperature and/or when the sensed metric indicative of blood flow meets or exceeds a metric threshold. In additional exemplary embodiments, such an alarm or signal may be initiated during a substantially continuous sub-skull temperature calculation operation where the rate of sub-skull temperature change meets or exceeds the predetermined sub-skull temperature change rate threshold.

Figure 8:
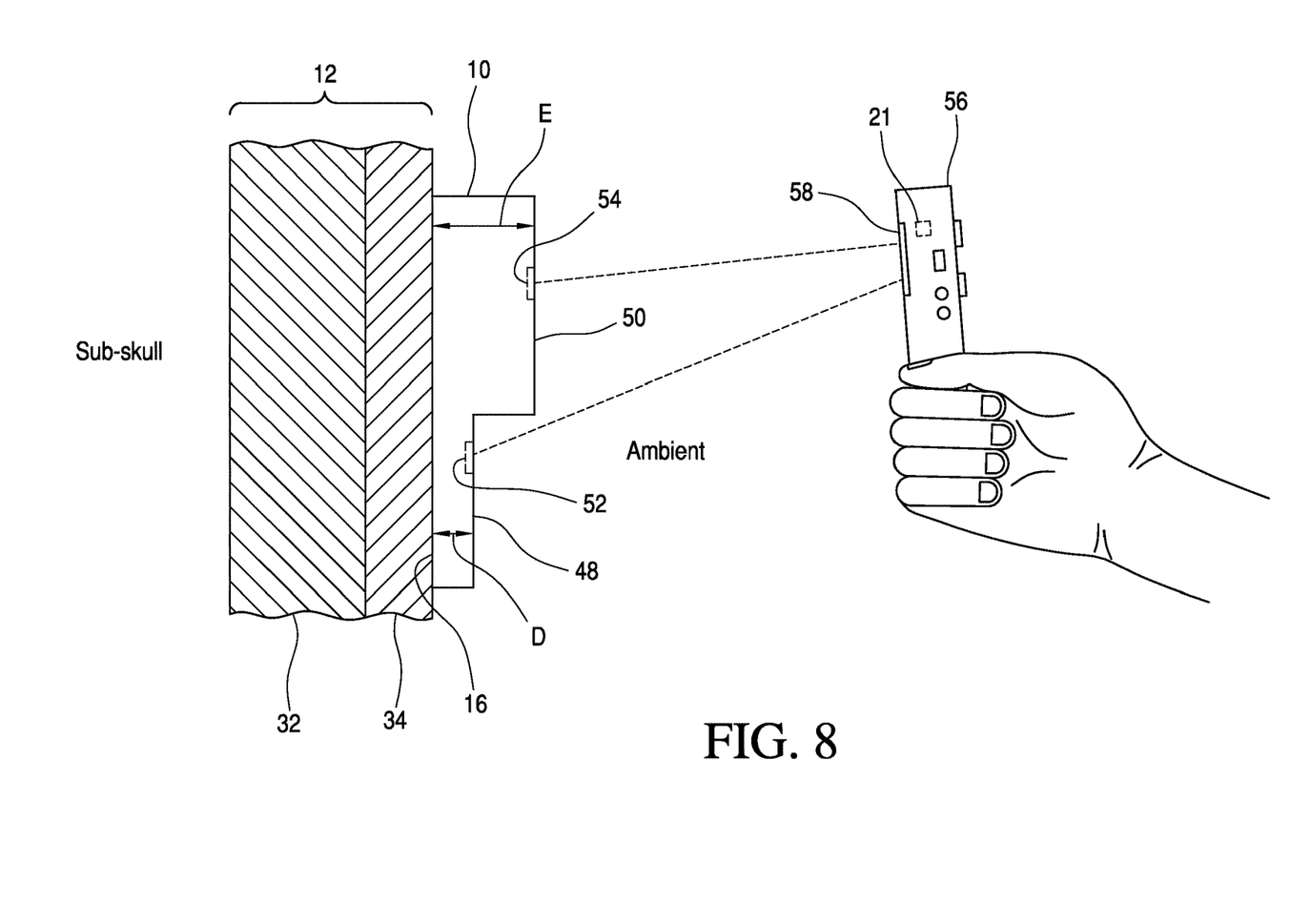
FIG. 8 illustrates a partial cross-section of a forehead of the subject with a patch connected thereto, according to still another exemplary embodiment of the present disclosure.

The patch 10 may further include one or more transponders 30. Such a transponder 30 may comprise, for example, one or more components configured to receive signals or information from a remote source, such as a remote controller 21 or the like. Such transponders 30 may also include one or more devices configured to transmit signals, data, and/or other information to remote receivers. For example, an exemplary transponder 30 may be configured to transmit information corresponding to one or more sensed temperatures to a remote computer, controller 21, or other like device utilized in the calculation of sub-skull temperatures of the subject 14. An exemplary remote controller 21 is illustrated in FIG. 8. Such exemplary transponders 30 may facilitate communication with remote devices using, for example, radio, infrared, wireless, WI-FI®, BLUETOOTH®, and/or other like technologies. Accordingly, such a transponder 30 may enable monitoring of subjects 14 fitted with the patch 10 from one or more remote locations within, for example, a hospital or other healthcare facility. In addition, such a transponder 30 may facilitate a wireless internet connection with one or more routers, servers, or the like.

In such an exemplary embodiment, the transponder 30 may enable a healthcare professional to monitor one or more conditions of the subject 14 remotely via a data and/or internet connection or the like. Although not shown in FIG. 2, it is understood that such a patch 10 may also include one or more USB ports, communication terminals, or other like components configured to facilitate connecting the patch 10 to one or more computers, controllers, monitors, servers, routers, or other like monitoring devices via one or more cables, wires, leads, or other like connection devices.

As previously discussed, the patch 10 may define at least two surfaces and, in an exemplary embodiment, the patch 10 may define a first surface 16 configured to at least temporarily contact and/or be removably attachable to the forehead 12 of the subject 14. The patch 10 may also include a second surface 18 disposed opposite the first surface 16 and configured to be exposed to ambient conditions such as, for example, to ambient air or other like environments in a hospital and/or other healthcare facility. As shown in at least FIG. 3, a first sensor 24 may be disposed at the first surface 16. In an exemplary embodiment, the sensor 24 may be embedded within the patch 10 so as to be integral with the patch 10. Alternatively, the sensor 24 may be substantially internal to the patch 10 such that the sensor 24 may be positioned and/or otherwise configured to sense a characteristic of the first surface 16. For example, the sensor 24 may be positioned and/or otherwise configured to sense a temperature of the first surface 16 of the patch 10 while the first surface 16 is in contact with and/or attached to the forehead 12. Such a sensor 24 may comprise, for example, a thermocouple, a thermistor, a thermometer, a resistance temperature detector (RTD), and/or any other like device useful in measuring temperature. In additional exemplary embodiments, such a sensor 24 may comprise any temperature sensitive material or coating known in the art.

In an exemplary embodiment, the sensor 24 may be substantially exposed to and/or disposed in contact with the skin 34 of the forehead 12 while the first surface 16 of the patch 10 is in contact with the forehead 12. Alternatively, the first surface 16 may include a relatively thin layer, wall, film, and/or other like barrier (not shown) extending between the skin 34 and the sensor 24 while the first surface 16 is in contact with the forehead 12. Such a barrier may form at least a portion of the first surface 16. In such an exemplary embodiment, the thermal resistance of such a barrier may be substantially negligible so as to maximize the accuracy of the one or more measurements made by the sensor 24. Alternatively, the thermal resistance of the barrier may be known or empirically determined, and this thermal resistance may be taken into account when calculating the sub-skull temperature of the subject 14. In additional exemplary embodiments, the sensor 24 may be configured to sense, measure, and/or otherwise detect one or more additional properties, conditions, and/or characteristics of the subject 14. For example, in addition to temperature, the sensor 24 may be configured to detect heart rate, blood pressure, electrical current, and the like.

The sensor 26 may be substantially identical to the sensor 24. As shown in, for example, FIGS. 2 and 3, the sensor 26 may be disposed at and/or proximate to the second surface 18. In an exemplary embodiment, the sensor 26 may be exposed to ambient conditions, while in additional exemplary embodiments, the second surface 18 may include a layer, wall, film, and/or barrier (not shown) similar to that described above with regard to the first surface 16. In such an exemplary embodiment, the barrier may extend between the sensor 26 and the ambient environment to protect the sensor 26 from contaminants, wet conditions, and/or other potentially damaging or harmful environmental elements. Similar to the barrier discussed above with regard to the first surface 16, a like barrier may form at least a portion of the second surface 18 and may have a substantially negligible thermal resistance so as not to hinder the accuracy of measurements obtained by the sensor 26. Alternatively, the thermal resistance of such a barrier may be taken into account when calculating the sub-skull temperature. Although shown in FIG. 3 as including two sensors 24, 26, in additional exemplary embodiments, the patch 10 may include any number of additional sensors configured to assist in sensing conditions of the subject 14 and/or the patch 10 such as temperature, blood pressure, heart rate, and/or other like metrics. Such additional sensors may be disposed at or along any of the surfaces 16, 18 of the patch 10 and/or at any other useful position along and/or within the patch 10.

The patch 10 may be made from any substantially rigid medically approved material known in the art. Such materials may include, for example, plastics, rubber, polymers, synthetic materials, cloth, mesh, and/or combinations thereof. For example, the patch 10 may be made from materials similar to removable bandages or other like materials. These materials may allow for breathability during use and for easy disposal once use is complete. In addition, such patch materials may be substantially flexible, substantially light-weight, and/or relatively comfortable such that a patch 10 may be disposed on and/or removably attached to the forehead 12 of a subject 14 for extended periods of time. To assist with such removable connection, any known adhesive may be disposed on at least a portion of the first surface 16. Alternatively, one or more elastic straps, headbands, belts, ties, or the like may be connected to at least a portion of the patch 10 to assist in removably attaching the patch 10 to the forehead 12.

The patch 10 may have a known thermal resistance, and such thermal resistance may depend upon, for example, the thickness A of the patch 10 as well as the one or more materials utilized to form the patch 10. The thermal resistance of the plastics, rubber, polymers, or other materials used to form the patch 10 may be known in the art, and the sub-skull temperature calculated in accordance with one or more of the exemplary methods described herein may be based upon the known thermal resistance of the patch 10.

As will be described in greater detail with regard to FIGS. 7 and 8, in exemplary embodiments of the present disclosure, the patch 10 may have one or more thicknesses. For example, a first portion 60 of the patch 10 may have a first thickness D between the first surface 16 and a second surface 48. A second portion 62 of such an exemplary patch 10 may also have a second thickness E between the first surface 16 and a third surface 50. Moreover, exemplary patches 10 of the present disclosure may be made from more than one material, and each portion of the patch 10 may have a unique thermal resistance depending upon the materials utilized to form the particular portion of the patch and/or the relative thickness of the portion. For example, the first portion 60 of the patch 10 shown in FIGS. 7 and 8 may be made from a first material and the second portion 62 of the patch 10 may be made from a second material different than the first material. In such an exemplary embodiment, the different portions 60, 62 of the patch 10 may have unique different thermal resistances. The different thermal resistances of each portion 60, 62 of the patch 10 may be taken into account when calculating, for example, the sub-skull temperature of the subject 14.

In an exemplary embodiment, a sub-skull temperature may be calculated by sensing one or more temperatures associated with the forehead skin 34 and/or patch 10 while the patch 10 is at least temporarily contacting and/or removably attached to the forehead 12. For example, in order to calculate a sub-skull temperature, a temperature of a surface of the patch 10 contacting the forehead 12 may be sensed along with a temperature of another surface of the patch 10 disposed away from the forehead 12. In additional exemplary embodiments, such temperature measurements may be taken at two different predetermined levels or depths within the various thicknesses of the patch 10, and along the heat transfer flow path. In such embodiments, the sensors 24, 26 may be positioned at such predetermined depths within the patch 10 for temperature measurement. According to basic heat transfer theory, the quantitative value of heat flow (q) is generally equal to the amount of heat energy passing through a given system over time. Such heat flow is governed by the resistance of the system as well as the temperature drop across the system. In the case of a subject 14, the core and/or sub-skull temperature of the subject 14 can be solved for utilizing these heat flow relationships.

In calculating the sub-skull temperature ($T_{sub\text{-}skull}$) of a subject 14, the temperature of the outer surface of the forehead skin 34 can be measured and/or otherwise sensed using a patch 10 disposed thereon. Alternatively, once the patch 10 has been disposed in contact with the forehead 12, the first surface 16 of the patch 10 may achieve substantially the same temperature as the outer surface of the forehead skin 34. Thus, in an alternative exemplary embodiment, the temperature of the first surface 16 of the patch 10 ($T_1$) may be sensed and, this surface temperature ($T_1$) may be utilized in the sub-skull temperature calculation.

In addition, a temperature of the second surface 18 of the patch 10 ($T_2$) disposed opposite the first surface 16 and away from the forehead 12 may also be sensed. As described above, the second surface 18 may be separated from the first surface 16 by the thickness A of the patch 10. The temperatures $T_1$, $T_2$ of the first and second surfaces 16, 18 may be used to calculate the amount of heat flowing out of the forehead 12, and thus the sub-skull temperature $T_{sub-skull}$ of the subject 14, according to the following equation:

$$T_{sub-skull}=T_1+R(T_1-T_2). \qquad [1]$$

In the above equation, "R" may be a constant that is estimated and/or empirically determined based upon the physical characteristics of the subject 14 and/or the patch 10. In particular, the constant R may be a thermal resistance associated with the skull 32 and/or skin 34 of the forehead 12. In an exemplary embodiment, the constant R may represent the thermal resistance of the forehead 12 consisting of both the skull 32 and skin 34. The value of the constant R utilized in the sub-skull temperature calculation may vary within a relatively limited range based on one or more physical characteristics of the subject 14. For example, a range of constants R may be estimated and/or empirically determined based upon at least one of the age, weight, gender, and/or other characteristics of the subject 14, and the values of such constants R may have a variation on the order of, approximately, 20%. In calculating the sub-skull temperature of a particular subject 14, a constant R may be chosen based upon whether the subject 14 is a small child, an average-sized adult, a large adult, and/or an elderly adult. In addition, the chosen constant R may vary for males as opposed to females, in any of the above age ranges or categories.

The value of each constant R may also be based upon the thermal resistance of the patch 10. The thermal resistance of the patch 10 may be dependent upon the physical construction and/or thermal characteristics of the patch 10 such as, for example, the materials used to form the patch 10 and/or the one or more thicknesses thereof. In an exemplary embodiment, the constant R may be calculated by dividing the thermal resistance of the forehead 12 by the thermal resistance of the patch 10. In exemplary embodiments, the constant R may be determined through experimentation and/or through one or more clinical trials utilizing different constructions and/or embodiments of the patch 10 to measure and/or calculate sub-skull temperature of subjects 14 having a variety of different ages, weights, genders, and/or other physical characteristics. A healthcare professional may then determine which constant R to use for a given subject 14 and patch 10 using one or more look-up tables or other like listings.

In additional exemplary embodiments, the calculated sub-skull temperature of the subject 14 may be based on one or more physical characteristics, conditions, and/or other metrics associated with the subject 14 and indicative of blood flow. For example, in calculating such a sub-skull temperature, a healthcare professional may measure, determine, and/or otherwise sense a metric indicative of blood flow at the forehead skin 34 of the subject 14. Significant blood flow proximate the first surface 16 of the patch 10 may cause error in temperature and/or other measurements obtained with the patch 10. For these reasons, it may be desirable and/or advantageous to avoid positioning the patch 10 proximate the temporal artery, or other veins or arteries of the subject 14. The forehead 12 of the subject 14 may be particularly well suited for calculating sub-skull temperature according to the exemplary methods described herein because the forehead 12 is generally free from such blood flow passageways. Accordingly, sensing a metric indicative of blood flow at the forehead skin 34 may assist in minimizing and/or substantially illuminating error in the sub-skull temperature calculation.

In exemplary embodiments in which the sensor 24 is disposed at and/or otherwise configured to sense a temperature of the first surface 16, it may be advantageous to sense the metric indicative of blood flow at an area of the forehead 12 proximate the first surface 16 of the patch 10. If the metric indicates an insignificant level of blood flow through the skin 34 that is proximate the first surface 16, the blood flow can be ignored in the calculation of sub-skull temperature. However, if the patch 10 is disposed at an area of the forehead 12 where significant blood flow is detected, the patch 10 may be repositioned on the forehead 12 to an area characterized by lower and/or insignificant blood flow levels. In further exemplary embodiments in which the metric indicates blood flow that is below a maximum threshold level requiring repositioning of the patch but that is above a minimum significance threshold, the metric may be taken into account when calculating the sub-skull temperature and the patch 10 may not be repositioned. Instead, as will be described below, the sensed metric may be used to generate a correction factor that can be incorporated into the sub-skull temperature calculation.

Figure 4:
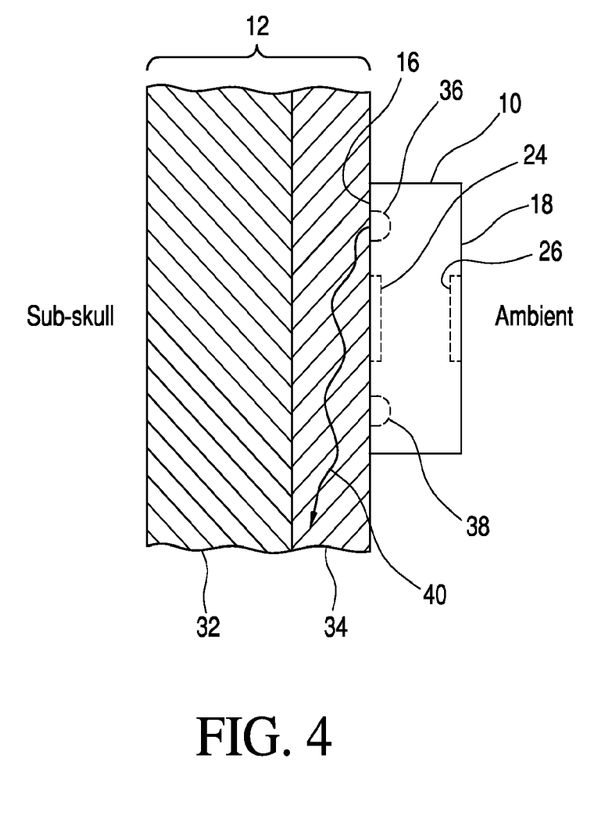
FIG. 4 illustrates a partial cross-section of a forehead of the subject with a patch connected thereto, according to another exemplary embodiment of the present disclosure.

In an exemplary embodiment, a periodic or pulsating change in the transmissivity of radiation passing through at least a portion of the forehead 12 may be used as a metric indicative of blood flow. For example, one or more beams of radiation may be passed through at least a portion of the forehead 12, and as such radiation passes through the forehead 12, the radiation may be slowed, deflected, defracted, reflected, and/or otherwise acted upon by components of the forehead and/or body functions or conditions of the subject 14. Such body functions may include, for example, arterial blood flow. As shown in FIG. 4, one or more beams of radiation 40 having a known wavelength may be passed through the skin 34 of the forehead 12 during an exemplary sub-skull temperature determination method. Such radiation 40 may then be detected and/or otherwise sensed as it passes along, beneath, and/or proximate to the first surface 16 of the patch 10. One or more characteristics of the radiation 40 may be altered as it passes through the skin 34, and the pulsating changes in such characteristics may be indicative of arterial blood flow through the skin 34 of the forehead 12. For example, significant levels of blood flow through the skin 34 may cause a corresponding relative change in the wavelength, frequency, amplitude, direction, and/or other characteristics of such radiation 40 as the radiation passes through the skin 34. Accordingly, detecting such radiation 40 passing through the skin 34 and/or determining the change in such radiation characteristics may be useful in determining the presence and/or amount of blood flow proximate the patch 10.

To facilitate the sensing of such a metric, an exemplary embodiment of the patch 10 may include, for example, at least one radiation source 36. The radiation source 36 may be, for example, an LED, a low power laser, an incandescent light bulb, and/or any other known light source configured to controllably emit radiation of a known wavelength, frequency, amplitude, and/or other controllable characteristic. In an exemplary embodiment, any known LED configured to emit radiation in the infrared spectrum, such as the Siemens SFH487 LED, may be employed. In other exemplary embodiments, the radiation source 36 may comprise, for example, a quantum cascade laser, or other known light source configured to emit radiation in the thermal band. Such radiation sources 36 may be shaped, sized, powered, and/or otherwise configured for safe usage proximate the skin 34 of the subject 14. For example, such radiation sources 36 may be configured for substantially direct contact with the skin 34 during use, and may be capable of substantially constant operation over relatively long periods of time without harming the skin 34 or causing discomfort to the subject 14.

In another exemplary embodiment, the sensed metric indicative of blood flow may be oxygen saturation. For example, the ratio of oxyhemoglobin to the total concentration of hemoglobin present in the blood may be sensed and/or otherwise measured at the skin 34 of the forehead 12, and a sub-skull temperature may be calculated based on such a metric. In such an exemplary embodiment, arterial oxyhemoglobin saturation may be measured using any of a number of non-invasive pulse oximetry devices using a reflective $SpO_2$ methodology. In such exemplary embodiments, the radiation source 36 may comprise or may be a component of any of a number of known oxygen saturation level measurement devices. Such devices may include a pulse oximeter or CO-oximeter, and in an exemplary embodiment, any known $SpO_2$ device such as the Nellcor™ Oximax™ Max-Fast™ forehead sensor may be employed. Such devices may be useful in providing non-invasive measurement of arterial blood oxygen saturation as well as pulse rate. Such devices may employ two or more radiation sources 36 to generate beams of infrared and/or other radiation 40 passing through the skin 34, venous vessels, bone, skull 32, and/or other body parts. Because variable amounts of such radiation 40 is absorbed and reflected as blood volume increases and decreases (during systole and diastole) the ratio of light absorption at systole and diastole may be translated into a measurement of oxygen saturation. Such a metric may then be utilized by methods of the present disclosure to indicate that the patch 10 should be repositioned and/or to assist in calculating the sub-skull temperature of the subject 14 due to indications of significant blood flow proximate the patch 10 in its current position.

In such exemplary embodiments, the patch 10 may also include one or more receivers 38 and/or other additional components of such oxygen saturation measurement devices. As shown in FIG. 4, such receivers 38 and/or other additional components may be disposed proximate the first surface 16 and/or may be otherwise embedded within the patch 10 to facilitate measurements proximate the first surface 16 and/or at the skin 34. In an exemplary embodiment, the receiver 38 may comprise one or more sensors, photo transistors, or other like detection devices configured to sense, detect, and/or otherwise measure the wavelength, frequency, amplitude, reflection, refraction, absorption, and/or other quantifiable characteristic of the radiation 40 emitted by the source 36. Any known sensor configured to measure the intensity of the reflected radiation 40, such as the Siemens SFH 309FA may be employed. For example, the receiver 38 and/or other components may be configured to instantaneously, periodically, and/or substantially continuously scan for blood flow and/or blood flow pulsations in the skin 34 proximate the first surface 16 of the patch 10.

In an exemplary sub-skull temperature calculation method, the patch shown in FIG. 4 may be removably attached to the forehead 12 of the subject 14, and the source 36 and receiver 40 may perform one or more reflective $SpO_2$ measurements of the type described above. If no arterial pulsations are detected, or if the sensed pulsations are indicative of blood flow below a minimum blood flow threshold, the patch 10 may be indicated to be disposed in an area where blood flow through the skin 34 will have substantially no impact on the calculated sub-skull temperature. Accordingly, equation [1] above can be used to accurately determine $T_{sub-skull}$ without repositioning the patch 10. In an exemplary embodiment, such a minimum threshold may correspond to $SpO_2$ pulsation intensity measurements equal to approximately 0.5%.

In such an exemplary embodiment, if the sensed pulsations are indicative of blood flow that is above a maximum threshold level, the controller may operate the display 22 and/or the signal device 28 to indicate that the patch 10 must be repositioned to an area of the forehead 12 characterized by less blood flow. In an exemplary embodiment, such a maximum threshold may correspond to $SpO_2$ pulsation intensity measurements equal to approximately 2.0%.

Moreover, in such an exemplary embodiment, if the sensed pulsations are indicative of blood flow that is greater than or equal to the minimum threshold discussed above and less than or equal to the maximum threshold, the intensity and/or other characteristics of the sensed pulsations may be used to add a correction factor to the sub-skull temperature calculation. Such a correction factor ($CF_p$) may compensate for heat flow (stray conduction) caused by blood moving through the skin 34 proximate the first surface 16. The amount of such stray conduction is a function of blood flow and near-surface blood temperature, and the correction factor $CF_p$ may be calculated according to the following equation:

$$CF_p = SC_p(\text{pulsation strength})(T_1 - T_2). \qquad [2]$$

In the above equation, "$SC_p$" may be an empirically derived constant converting the pulsatile blood flow measurement to a temperature adjustment due to stray conduction effects. In addition, "pulsation strength" may be a percentage or other arterial blood flow value sensed and/or output during the above $SpO_2$ measurements. Thus, in such an exemplary embodiment, equation [1] above can be modified to calculate sub-skull temperature as follows:

$$T_{sub-skull} = T_1 + R(T_1 - T_2) + CF_p. \qquad [3]$$

In still another exemplary embodiment of the present disclosure, a metric indicative of blood flow at and/or otherwise through the forehead skin 34 may include one or more temperature gradients caused by and/or resulting from substantially lateral blood flow through the skin 34. Because blood flow through the forehead skin 34 is typically directional, a temperature gradient may be observed, measured, and/or otherwise sensed at the skin 34 proximate the first surface 16 of the patch 10. In an exemplary embodiment, such a temperature gradient may be sensed across the first surface 16 even after the patch 10 has been attached and/or disposed in contact with the skin 34 for a time sufficient for the patch 10 to reach a level of substantial thermal stability.

In such an exemplary embodiment, relatively minimal blood flow may result in a corresponding temperature gradient of minimal magnitude. However, more substantial blood flow through the skin 34 at the forehead 12 may result in a temperature gradient that is correspondingly larger in magnitude. As described above with, for example, the embodiment of FIG. 4, a temperature gradient sensed across the first surface 16 of the patch 10 may be taken into account in determining whether the patch 10 should be repositioned on the forehead 10 and/or when calculating a sub-skull temperature of the subject 14. Accounting for the presence and/or strength of such a temperature gradient may increase the accuracy of sub-skull temperature calculations.

In an exemplary embodiment, one or more temperatures may be substantially continuously sensed at a plurality of locations along the first surface 16. In such an exemplary embodiment, a temperature gradient and/or difference sensed between any two points along the first surface 16 may be indicative of the existence of blood flow and/or the amount or volume of blood flow proximate the first surface 16. Sensing such temperatures at a plurality of locations along the first surface 16 may also be useful in evaluating the direction of blood flow through the skin 34.

Figure 5:
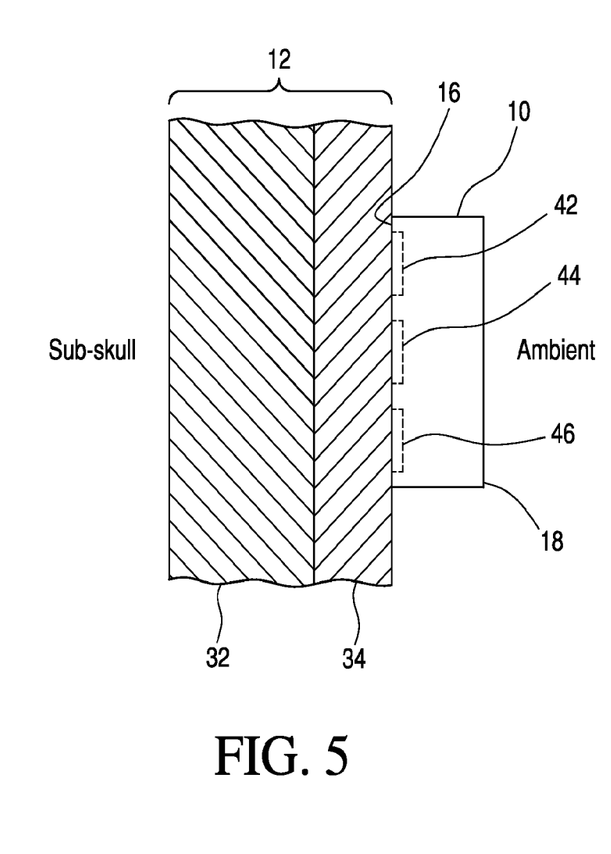
FIG. 5 illustrates a partial cross-section of a forehead of the subject with a patch connected thereto, according to still another exemplary embodiment of the present disclosure.
Figure 6:
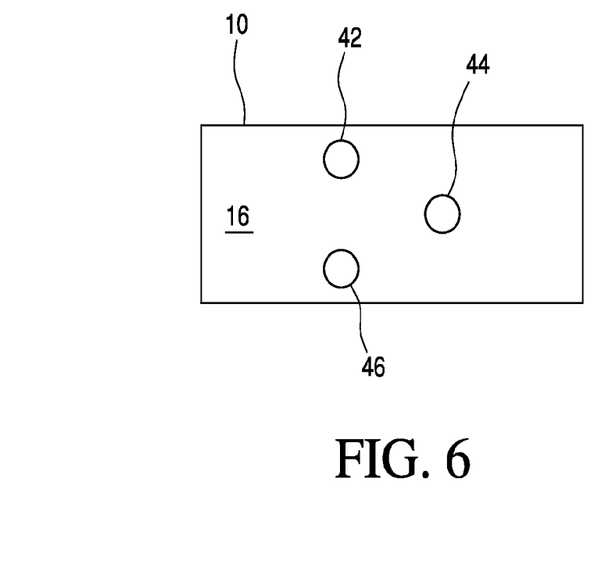
FIG. 6 illustrates a first surface of the patch according to an exemplary embodiment of the present disclosure.

As shown in FIGS. 5 and 6, the patch 10 may include more than one sensor disposed at and/or proximate to the first surface 16. For example, the patch 10 may include a plurality of sensors 42, 44, 46 disposed at a different location along the first surface 16. In an exemplary embodiment, such sensors 42, 44, 46 may be disposed proximate a periphery of the first surface 16 and/or may be optimally spaced along the first surface 16 to maximize the area of the skin 34 capable of being sensed. Such spacing may also maximize the ability of the sensors 42, 44, 46 to evaluate blood flow in multiple different directions through the skin 34. The sensors 42, 44, 46 may comprise, for example, any known thermocouple, thermistor, thermometer, RTD, temperature sensitive material, temperature sensitive coating, and/or light sensing device, and in an exemplary embodiment, the sensors 42, 44, 46 may be substantially similar to the sensors 24, 26 described above. In an exemplary embodiment in which the patch 10 includes more than one sensor 42, 44, 46 disposed at and/or proximate to the first surface 16, the sensor 24 described above may be one of the sensors 42, 44, 46. Such sensors 42, 44, 46 may also be electrically, controllably, and/or otherwise operably connected to the controller (not shown) of the patch 10 described herein. Although shown in a substantially triangular arrangement in FIG. 6, it is understood that the sensors 42, 44, 46 may be arranged in any pattern and/or other configuration along the first surface 16. For example, in additional exemplary embodiments, the patch 10 may include any number of additional sensors along the first surface 16, and such sensors may be arranged in a circular pattern. Alternatively, the patch 10 may include at least one sensor disposed at each corner of the first surface 16 to assist in observing and/or otherwise sensing a temperature gradient along the first surface 16.

In an exemplary sub-skull temperature calculation method, the patch 10 shown in FIGS. 5 and 6 may be removably attached to the forehead 12 of the subject 14, and the multiple sensors 42, 44, 46 disposed at the first surface 16 of the patch 10 may instantaneously and/or substantially continuously sense the temperature of the first surface 16 at the various respective sensor locations. Information corresponding to these sensed temperatures may then be sent to the controller. If substantially no measurable difference in temperature is sensed among the various sensors 42, 44, 46, or if the greatest difference between the various sensed temperatures is below a minimum temperature difference threshold, the patch 10 may be disposed in an area of the forehead 12 where blood flow through the skin 34 may have substantially no impact on the calculated sub-skull temperature. Accordingly, equation [1] above may be used to accurately determine the sub-skull temperature without repositioning the patch 10 on the forehead 12. In an exemplary embodiment, such a minimum threshold may be, approximately 0.5° F.

In such an exemplary embodiment, if the difference between the lowest sensed temperature and the highest sensed temperature is above a maximum temperature difference threshold, such a detected temperature gradient may be indicative of blood flow levels that may cause an unacceptable level of error in the sub-skull temperature calculation. If such a difference exists, the controller may operate the display 22 and/or the signal device 28 to indicate that the patch 10 must be repositioned to an area of the forehead 12 characterized by less blood flow. In an exemplary embodiment, such a maximum threshold may be approximately 1.5° F.

Moreover, in such an exemplary embodiment, if the difference between the lowest sensed temperature and the highest sensed temperature is greater than or equal to the minimum temperature difference threshold discussed above and less than or equal to the maximum temperature difference threshold, such a detected temperature difference and/or gradient may be used to add a correction factor to the sub-skull temperature calculation similar to the correction factor CFp discussed above with regard to the exemplary embodiment of FIG. 4. For example, the amount of heat flow (stray conduction) caused by blood moving through the skin 34 proximate the first surface 16 can be estimated using the sensed cross-patch temperature gradient detected by the sensors 42, 44, 46. Similar to the process described above with regard to FIG. 4, in the exemplary embodiment of FIG. 6, equation [1] above can be modified to calculate sub-skull temperature as follows:

$$T_{sub\text{-}skull} = T_1 + R(T_1 - T_2) + CF_t. \quad [4]$$

In the above equation, the correction factor "$CF_t$" may compensate for heat flow (stray conduction) caused by blood flow moving through the skin 34, and the correction factor $CF_t$ may be calculated according to the following equation:

$$CF_t = SC_t(\Delta_{Tmax})(T_1 - T_2). \quad [5]$$

In the above equation, "$SC_t$" may be an empirically derived constant converting the cross-patch temperature gradient to a temperature adjustment due to stray conduction effects. In addition, "$\Delta_{Tmax}$" may be the difference between the lowest sensed temperature and the highest sensed temperature.

In additional exemplary embodiments, a sub-skull temperature of the subject 14 may be calculated based on sensed temperatures of two or more surfaces of the patch 10 that are spaced from and/or otherwise not in direct physical contact with the skin 34 of the forehead 12. In such an exemplary embodiment, the first surface 16 of the patch 10 may be removably attached to the skin 34 of the forehead 12 as described above. As shown in FIGS. 7 and 8, such an exemplary patch 10 may include two or more portions 60, 62 having different respective thicknesses. For example, the first portion 60 of the patch 10 may have a thickness D, and this first portion 60 may define a second surface 48 that is separated from the first surface 16 by the thickness D. In addition, the second portion 62 of such an exemplary patch 10 may define a second patch thickness E that is different than the first patch thickness D. The second portion 62 may define a third surface 50 that is spaced from the first surface 16 by the thickness E. As shown in FIGS. 7 and 8, the second surface 48 may be disposed substantially parallel to the third surface 50, and both surfaces 48, 50 may be disposed substantially parallel to the first surface 16. Alternatively, in additional exemplary embodiments, the second surface 48 may be disposed at any obtuse or acute angle relative to the third surface 50. In addition, the second and third surfaces 48, 50 may be disposed at any desirable angle relative to the first surface 16.

Any of the patches 10 described herein may be made from more than one material. Such exemplary patches 10 may define a single substantially uniform thickness, or alternatively, various portions of the patch 10 made from different materials may have unique different thickness and/or thermal resistances. For example, the patch 10 illustrated in FIGS. 7 and 8 may be made from at least one material and, in further exemplary embodiments, the first portion 60 of the patch 10 associated with the second surface 48 may be made from a first material, and the second portion 62 of the patch 10 associated with the third surface 50 may be made from a second material different than the first material. The patch 10 illustrated in FIGS. 7 and 8 may be made from one or more of the materials described above with regard to the patches 10 of previous embodiments, and in the exemplary embodiment of FIGS. 7 and 8, the first thickness D and/or the first portion 60 of the patch 10 defining the second surface 48 may be characterized by a first thermal resistance. In addition, the second thickness E and/or the second portion 62 of the patch 10 defining the third surface 50 may be characterized by a second thermal resistance that is different from the first thermal resistance of thickness D. In additional exemplary embodiments, a patch 10 having a single substantially uniform thickness may be made from two or more different materials, each characterized by different respective thermal resistances. Thus, a patch 10 having different portions characterized by different respective thermal resistances may be formed and/or achieved by material selection and/or thickness selection. In calculating a sub-skull temperature utilizing a patch 10 having portions characterized by more than one thermal resistance, such as the exemplary patch 10 illustrated in FIGS. 7 and 8, the respective different thermal resistances may each be taken into account. Such a calculation may be accomplished utilizing, for example, equations [6] or [7] below.

In addition to calculating a sub-skull temperature based on the different thermal resistances of portions 60, 62, such a calculation may also be based on sensed temperatures of the second and third surfaces 48, 50. In such an exemplary embodiment, the temperatures of the second and third surfaces 48, 50 may be sensed while the first surface 16 is connected and/or removably attached to the forehead 12 of the subject 14. As shown in FIG. 7, an exemplary embodiment of the patch 10 may include a sensor 26 disposed at and/or otherwise associated with the second surface 48 and another sensor 28 disposed at and/or otherwise associated with the third surface 50. As described above, such sensors 26, 28 may be electrically, controllably, and/or otherwise operably connected to a controller (not shown) of the exemplary patch 10, so as to assist in sensing the temperature of the second and third surfaces 48, 50 and calculating the sub-skull temperature of the subject 14. In particular, in the embodiment of FIG. 7, the sensor 26 may be configured to sense a temperature of the second surface 48 ($T_{second\ surface}$), and the sensor 28 may be configured to sense the temperature of the third surface 50 ($T_{third\ surface}$). These two patch surface temperatures, as well as an estimated thermal resistance R of the subject's skull 32 and forehead skin 34 may be utilized to calculate an exemplary sub-skull temperature. Such a calculation my be accomplished utilizing, for example, the equations:

$$T_{sub\text{-}skull} = T_{third\ surface} + R(T_{third\ surface} - T_{second\ surface}),\quad [6]$$

or $$T_{sub\text{-}skull} = T_{second\ surface} + R(T_{third\ surface} - T_{second\ surface}). \quad [7]$$

Figure 7:
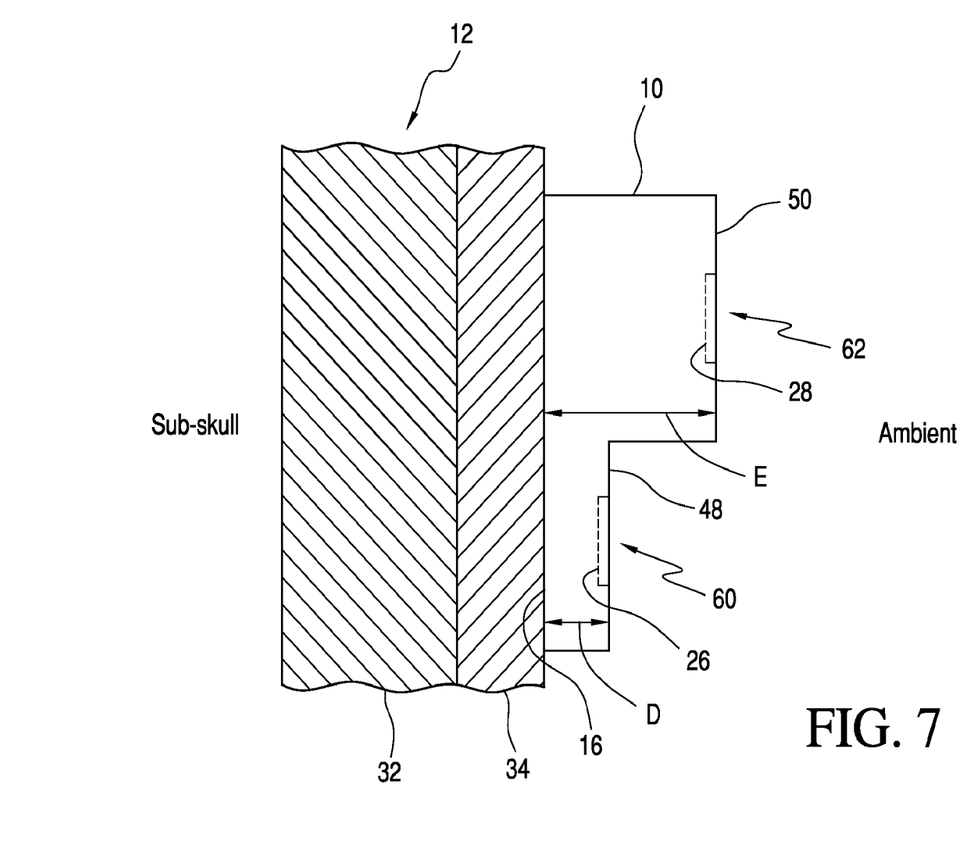
FIG. 7 illustrates a partial cross-section of a forehead of the subject with a patch connected thereto, according to another exemplary embodiment of the present disclosure.

As shown in FIG. 8, in additional exemplary embodiments, one or both of the sensors 26, 28 shown in FIG. 7 may be omitted. For example, the respective temperatures of the second surface 48 ($T_{second\ surface}$) and third surface 50 ($T_{third\ surface}$) may still be utilized to calculate the sub-skull temperature of the subject 14, however, in the embodiment of FIG. 8, the two surface temperatures may be sensed utilizing any of a number of known non-contact thermometry methods. For example, a non-contact sensing device 56 may be employed to detect the respective temperatures of the second and third surfaces 48, 50. In such an exemplary embodiment, the sensing device 56 may include one or more sensors 58 configured to acquire such temperatures without contacting the respective surfaces 48, 50. In such an exemplary embodiment, the device 56 may include any known infrared thermometry device configured to assist in obtaining such temperatures.

In such an exemplary embodiment, the patch 10 may define one or more targets 52, 54 associated with the respective surfaces 48, 50 to assist in sensing the temperature of these surfaces. Such targets 52, 54 may comprise, for example, one or more notches, cut-outs, divots, dimples, bubbles, ridges, flats, shoulders, and/or any other substantially planar, substantially convex, and/or substantially concave structure useful in assisting the non-contact sensing device 56 in obtaining an accurate temperature measurement. Moreover, the one or more sensor 58 associated with the non-contact sensing device 56 may be configured to sense one or more characteristics of the ambient environment in which the patch 10 is being used. In such an exemplary embodiment, the sub-skull temperature of the subject 14 may be calculated by controller 21 utilizing the following equation:

$$T_{sub\text{-}skull} = T_{third\ surface} - T_{second\ surface} * (R1/R2) \\ ((T_{second\ surface} - T_{ambient})/(T_{third\ surface} - T_{ambient}))/((1-(R1/R2)*((T_{second\ surface} - T_{ambient})/(T_{third\ surface} - T_{ambient}))). \quad [8]$$

In the above equation, it is understood that "R1" represents the combined thermal resistance of the forehead 12 and thickness D, "R2" represents the combined thermal resistance of the forehead 12 and thickness E, and "$T_{ambient}$" represents the ambient temperature measured by, for example, the sensor 58.

The invention has been described in detail with particular reference to a presently preferred embodiment, but it will be understood that variations and modifications can be effected within the spirit and scope of the invention. The presently disclosed embodiments are, therefore, considered in all respects to be illustrative and not restrictive. The scope of the invention is indicated by the appended claims, and all changes that come within the meaning and range of equivalents thereof are intended to be embraced therein.

The invention claimed is:
1. A temperature determination device, comprising:
   a patch defining a first surface and a second surface opposite the first surface, wherein the first surface is removably attachable to skin of a subject at a first location of the subject's skin;
   a first temperature sensor connected to the patch and configured to detect a temperature of the first surface;

a second temperature sensor connected to the patch and configured to detect a temperature of the second surface; and at least one additional electronic sensing component connected to the patch and configured to determine a metric, other than temperature, indicative of a first amount of blood flow proximate the first location, wherein a controller in communication with the device is programmed to:

receive a first signal from the at least one additional electronic sensing component indicative of the metric as determined by the at least one additional electronic sensing component while the patch is disposed at the first location, compare the metric to a threshold corresponding to the metric, determine, based at least partly on comparing the metric to the threshold, that the patch should be repositioned to a second location of the subject's skin characterized by a second amount of blood flow less than the first amount, wherein determining that the patch should be repositioned includes:
determining that the metric exceeds the threshold, and
operating an operator interface device to indicate that the patch should be repositioned, receive a second signal from the at least one additional electronic sensing component indicative of the metric as determined by the at least one additional electronic sensing component after the patch has been repositioned to the second location, determine, based at least partly on the second signal, that the metric as determined by the at least one additional electronic sensing component after the patch has been repositioned to the second location is less than or equal to the threshold, and calculate, at least partly in response to determining that the metric as determined by the at least one additional electronic sensing component after the patch has been repositioned to the second location is less than or equal to the threshold, a core temperature of the subject based on the temperature of the first surface, the temperature of the second surface, and an estimated thermal resistance of the subject's skin.

2. The device of claim 1, wherein the controller is operably connected to the first temperature sensor, the second temperature sensor, and the at least one additional electronic sensing component, the controller being configured to
calculate the core temperature based on the detected temperatures of the first and second surfaces, the estimated thermal resistance of the subject's skin, and a known thermal resistance of the patch.

3. The device of claim 1, wherein the at least one additional electronic sensing component comprises an infrared radiation source and a third sensor, the third sensor being configured to detect radiation emitted by the radiation source.

4. The device of claim 1, wherein the patch further includes a third surface opposite the first surface, the second surface being separated from the first surface by a first patch thickness, and the third surface being separated from the first surface by a second patch thickness different than the first patch thickness.

5. The device of claim 4, wherein the first thickness is characterized by a first thermal resistance and the second thickness is characterized by a second thermal resistance different than the first thermal resistance.

6. The device of claim 4, wherein a first portion of the patch comprising the first thickness is made from a first material, and wherein a second portion of the patch comprising the second thickness is made from a second material different than the first material.

7. The device of claim 1, wherein the patch includes at least one additional sensor positioned to detect the temperature of the first surface, wherein the first temperature sensor is spaced from the at least one additional sensor such that the first temperature sensor and the at least one additional sensor are configured to determine a direction of blood flow proximate the first location and relative to the first surface.

8. The device of claim 7, wherein the first temperature sensor is disposed at a first location on the first surface and the at least one additional sensor is positioned at a second location on the first surface different than the first location, the first temperature sensor being configured to detect a temperature of the first location, the at least one additional sensor being configured to detect a temperature of the second location, and the device being configured to determine that a difference between the temperature of the first location and the temperature of the second location is greater than a temperature difference threshold.

9. The device of claim 8, wherein the operator interface device comprises at least one of a display or a signal device operably connected to the controller and configured to indicate that the difference is greater than the temperature difference threshold.

10. The device of claim 1, further comprising a transponder operably connected to at least one of the first temperature sensor or the second temperature sensor, wherein the transponder is configured to wirelessly transmit information corresponding to at least one of the temperature of the first surface or the temperature of the second surface.

11. The device of claim 10, wherein the transponder comprises a radio transponder.

12. The device of claim 1, wherein the at least one additional electronic sensing component comprises an $SpO_2$ sensor configured to determine at least one of arterial blood oxygen saturation or pulse rate of the subject.

13. The device of claim 1, wherein the controller is programmed to calculate the core temperature of the subject based on:
the temperature of the first surface as determined after the patch has been repositioned to the second location,
the temperature of the second surface as determined after the patch has been repositioned to the second location, and
the estimated thermal resistance of the subject's skin.

14. The device of claim 1, wherein the first location is a first distance from the temporal artery of the subject and the second location is a second distance from the temporal artery greater than the first distance.

15. A method of manufacturing a measurement device, comprising:
providing a patch defining a first surface and a second surface opposite the first surface, wherein the first surface is removably attachable to skin of a subject at a first location of the subject's skin;
operably connecting a first temperature sensor to the patch proximate the first surface, the first temperature sensor being positioned to detect a temperature of the first surface;

operably connecting a second temperature sensor to the patch proximate the second surface, the second temperature sensor being positioned to detect a temperature of the second surface;

operably connecting at least one additional electronic sensing component to the patch, the at least one additional electronic sensing component being configured to determine a metric, other than temperature, indicative of a first amount of blood flow proximate the first location; and operably connecting the first temperature sensor, the second temperature sensor, and the at least one additional electronic sensing component to a controller, wherein the controller is programmed to:
receive a first signal from the at least one additional electronic sensing component indicative of the metric as determined by the at least one additional electronic sensing component while the patch is disposed at the first location,
compare the metric to a threshold corresponding to the metric,
determine, based at least partly on comparing the metric to the threshold, that the patch should be repositioned to a second location of the subject's skin characterized by a second amount of blood flow less than the first amount, wherein determining that the patch should be repositioned includes:
determining that the metric exceeds the threshold, and
operating an operator interface device to indicate that the patch should be repositioned,
receive a second signal from the at least one additional electronic sensing component indicative of the metric as determined by the at least one additional electronic sensing component after the patch has been repositioned to the second location,
determine, based at least partly on the second signal, that the metric as determined by the at least one additional electronic sensing component after the patch has been repositioned to the second location is less than or equal to the threshold, and
calculate, at least partly in response to determining that the metric as determined by the at least one additional electronic sensing component after the patch has been repositioned to the second location is less than or equal to the threshold, a core temperature of the subject based on the temperature of the first surface, the temperature of the second surface, and an estimated thermal resistance of the subject's skin.

16. The method of claim 15, wherein the controller is configured to calculate the core temperature based on the detected temperatures of the first and second surfaces, the estimated thermal resistance of the subject's skin, and a known thermal resistance of the patch.

17. The method of claim 15, further including forming a third surface of the patch opposite the first surface, the second surface being separated from the first surface by a first patch thickness, and the third surface being separated from the first surface by a second patch thickness different than the first patch thickness.

18. The method of claim 17, further comprising forming a first portion of the patch, comprising the first thickness, from a first material, and forming a second portion of the patch, comprising the second thickness, from a second material different than the first material.

19. The method of claim 15, further comprising operably connecting a transponder to at least one of the first temperature sensor or the second temperature sensor, wherein the transponder is configured to wirelessly transmit information corresponding to at least one of the temperature of the first surface or the temperature of the second surface.

20. The method of claim 15, wherein the at least one additional electronic sensing component comprises an $SpO_2$ sensor configured to determine at least one of arterial blood oxygen saturation or pulse rate of the subject.

21. A method of determining a core temperature of a subject, comprising:
removably disposing a first surface of a patch at a first skin location on skin of the subject;
exposing a second surface of the patch opposite the first surface to ambient conditions;
determining a first temperature of a first location on the patch while the first surface is disposed on the skin at the first skin location;
determining a second temperature of a second location on the patch while the first surface is disposed on the skin at the first skin location, the first location being different than the second location;
determining a first value of a metric, other than temperature, indicative of a first amount of blood flow proximate the first skin location;
comparing the first value of the metric to a threshold;
determining, with a controller associated with the device and based at least partly on comparing the first value of the metric to the threshold, the patch should be repositioned to a second skin location on the subject's skin characterized by a second amount of blood flow less than the first amount, wherein the controller is programmed to calculate the core temperature of the subject;
operating an operator interface to indicate that the patch should be repositioned;
determining a second value of the metric, the second value of the metric being indicative of a second amount of blood flow proximate the second skin location after the patch has been repositioned to the second skin location;
comparing the second value of the metric to the threshold;
determining, with the controller and based at least partly on comparing the second value of the metric to the threshold, that the patch may remain at the second skin location; and
calculating, with the controller and at least partly in response to determining that the patch may remain at the second skin location, the core temperature of the subject, wherein the core temperature is calculated based on the first temperature, the second temperature, and an estimated thermal resistance of the subject's skin, wherein the first and second temperatures are determined without contacting the patch.

22. The method of claim 21, wherein the controller comprises a component of a non-contact sensing device separate from the patch, the first temperature comprises a temperature of the second surface, and the second temperature comprises a temperature of a third surface of the patch opposite the first surface.

23. The method of claim 21, wherein determining the first and second temperatures comprises detecting the first and second temperatures after the patch has been repositioned to the second skin location.

24. The method of claim 21, wherein the patch has a first thickness at the first location and a second thickness at the second location, the first thickness being different than the second thickness.

25. The method of claim 21, wherein the metric comprises at least one of arterial blood oxygen saturation or pulse rate of the subject, and wirelessly transmitting the at least one of arterial blood oxygen saturation or pulse rate via a transponder of the patch.

26. The method of claim 25, wherein the at least one of the arterial blood oxygen saturation or the pulse rate is transmitted via wireless communication.

* * * * *